United States Patent [19]

Shinkawa et al.

[11] Patent Number: 4,938,930
[45] Date of Patent: Jul. 3, 1990

[54] REACTION VESSEL

[75] Inventors: Toshikazu Shinkawa; Daisaku Shozen; Kazuto Kobayashi; Hiroshi Makihara, all of Hiroshima; Kensuke Niwa, Tokyo; Kazuhiro Morita, Tokyo; Masaaki Kuwa, Niigata; Murayama Katsutoshi, Niigata, all of Japan

[73] Assignees: Mitsubishi Jukogyo Kabushiki Kaisha; Mitsubishi Gas Chemical Company, Inc., both of Tokyo, Japan

[21] Appl. No.: 96,810

[22] Filed: Sep. 10, 1987

Related U.S. Application Data

[63] Continuation of Ser. No. 819,507, filed as PCT JP85/00227 on Apr. 23, 1985, published as WO85/04820 on Nov. 7, 1985, abandoned.

[30] Foreign Application Priority Data

Apr. 23, 1984 [JP] Japan .................................. 59-80053

[51] Int. Cl.$^5$ ............................................... B01J 8/06
[52] U.S. Cl. .................................... 422/197; 422/148; 422/202; 422/216; 422/220
[58] Field of Search ............... 422/197, 198, 202, 216, 422/220, 148

[56] References Cited

U.S. PATENT DOCUMENTS 3,050,377 8/1962 Christensen .
4,205,044 5/1980 Gramatica ...................... 422/192 X
4,346,060 8/1982 Eagle et al. ...................... 422/198 X
4,411,870 10/1983 Kroushl et al. .................. 422/197 X

FOREIGN PATENT DOCUMENTS 155851 4/1943 Japan .
57-38568 3/1982 Japan .
58-21724 12/1983 Japan .

Primary Examiner—Barry S. Richman
Assistant Examiner—Jill Johnson
Attorney, Agent, or Firm—Fleit, Jacobson, Cohn, Price, Holman & Stern

[57] ABSTRACT

A reaction vessel has a catalytic core, with an inlet for a first gas and for a second gas. The first and second gasses react in an exothermic reaction during passage through the catalytic core. The first gas passes through conduits which extend through the catalytic core, so as to be preheated and also so as to cool the catalytic core so that the catalyzed reaction proceeds in a preferred temperature range. The gasses are mixed at one end of the vessel in a mixing chamber, and are drawn through the catalytic core into a gathering chamber, from which the reacted gasses exit. A cooling chamber is provided for introduction of a cooling fluid about the periphery of the catalytic core, for drawing away any excess heat during operation.

3 Claims, 5 Drawing Sheets

REACTION VESSEL

CROSS REFERENCE TO RELATED APPLICATIONS

This is a continuation of application Ser. No. 819,507, filed as PCT JP85/00227 on Apr. 23, 1985 as WO85/04820 on Nov. 7, 1985 now abandoned.

TECHNICAL FIELD

The present invention relates to an improved reaction vessel which is used to carry out an exothermic reaction of a mixed gas consisting of a plurality of elements in the presence of a solid catalyst, as in the case of a synthesis of methanol from hydrogen and a carbon monoxide (and carbon dioxide) gas.

BACKGROUND TECHNOLOGY

As reaction vessels of this type, there have been suggested ones involving means or structures for controlling the rise of a gas temperature resulting from an exothermic reaction during operation. FIG. 1 attached hereto exemplarily shows the effect of a temperature on a methanol equilibrium concentration in a methanol synthesis reaction, and as is definite from it, the methanol equilibrium concentration will be low along with the rise of the temperature, so that an economy of an industrial plant will be impaired. Therefore, the above-mentioned suggested reaction vessels have attempted to eliminate such a disadvantage. FIG. 1 above has been quoted from "Methanol", Nozawa, Vol. 46, No. 9, p. 507 (1982) and calculated values have been obtained by setting, to 4, a ratio of $H_2$ to CO in the reaction of $CO+2H_2 \rightarrow CH_3OH$. In this reaction, a reaction rate is limited even if a catalyst is employed, but naturally the reaction rate will be low with the fall of the temperature. Therefore, it is industrially preferred that the operation of the reaction vessel is carried out within a certain proper temperature range in view of catalyst performance. In the case of synthesizing methanol from a mixed gas containing hydrogen, carbon monoxide and carbon dioxide as major component materials by the use of a copper catalyst, the inventors of the present application have the understanding that a preferred temperature lies within the range of 220° to 280° C. and a preferred and economical pressure (total pressure) of the gas lies within the range of 50 to 300 kg/cm$^2$•G, but these preferred ranges can vary dependent upon any future improvement in the catalysts used.

A known method for adjusting this temperature is disclosed in, for example, Japanese Patent Publication No. 38568/1982.

This known technique, as shown in FIG. 2, comprises causing a pressurized mixed gas, i.e., an unreacted gas A consisting of hydrogen, carbon monoxide, carbon dioxide and the like which has previously been heated to a suitable temperature, to flow through a catalyst filling reaction pipe 2 in a reaction vessel 1 upward from a lower position thereof in order to accomplish a methanol synthesis reaction, and getting rid of the resultant reaction heat via the latent evaporation latent heat of water, having a suitable pressure and a saturated temperature, which is brought into contact with the outer surface of the reaction pipe, whereby a temperature of the mixed gas in the reaction pipe is maintained in a suitable condition range. In FIG. 2, reference symbol B represents a reaction gas, and numerals 3 and 4 are water to be supplied and water vapor to be discharged, respectively. Practically, a number of reaction pipes can be disposed therein, but in FIG. 2, simplification is made for clarity.

In the case of the above known example, however, it is necessary to previously heat, by a heat exchanger, the feed gas which will be forwarded to the reaction vessel, which fact means that it is poor in economy. Further, as is definite from FIG. 3 which is a sectional view of the reaction pipe 2 in FIG. 2, the pipe 2 is packed with a grainy catalyst 4 in the form of a column, therefore the central portion of the catalyst layer 4 is so considerably away from the heat transmitting surface that a sufficient cooling (control of a reaction temperature of the gas, i.e, maintenance of an optimum temperature) is disadvantageously difficult to achieve.

The present inventors have already suggested a double pipe type exothermic reaction vessel by which the above-mentioned drawbacks are eliminated (Japanese Patent Application No 213724/1983), but the present invention intends to provide a further improved reaction vessel.

SUMMARY OF THE INVENTION

The present inventors have invented the following apparatus: A reaction pipe 2 is constructed in the form of a double pipe as shown in FIG. 4, and a circular space between an outer pipe 2' and an inner pipe 2" is packed with a grainy catalyst 4, so that the catalyst layer is thin. An outside surface of the outer tube 2' is cooled with cooling water and an inside surface of the inner tube 2" is cooled with an unreacted feed gas A so as to maintain a temperature of the gas at a proper level within the narrow temperature range in a direction across the catalyst layer and to simultaneously preheat the unreacted feed gas A. It has been found that such a constitution is advantageous for the control of the reaction temperature, leads to the effect of rendering needless a heat exchanger for preheating the unreacted feed gas, permits lowering a temperature at an inlet of the catalyst layer by mixing the unreacted feed gas preheated ascending through a central pipe with a cold unreacted feed gas, and can suitably adjust a temperature of the catalyst layer.

That is to say, the present invention is directed to a reaction vessel for an exothermic reaction which comprises a plurality of reaction pipes, central pipes disposed in the middle of the reaction pipes, and circular catalyst layers formed by packing circular spaces defined between the reaction pipes and the central pipes with a grainy catalyst, whereby an unreacted feed gas can be caused to flow through the central pipes upward from lower positions thereof and can be then caused to flow through the circular catalyst layers downward from upper positions thereof, the central pipes through which the unreacted feed gas flows being connected to one or more mixing chambers defined at an upper portion in the reaction vessel, the mixing chamber being provided with an inlet for allowing a cold unreacted feed gas to pass therethrough, which cold gas having a lower temperature than the unreacted feed gas coming out from the central pipes.

DETAILED DESCRIPTION OF THE INVENTION

The present invention will be described in detail in reference to accompanying drawings.

Figure 1:
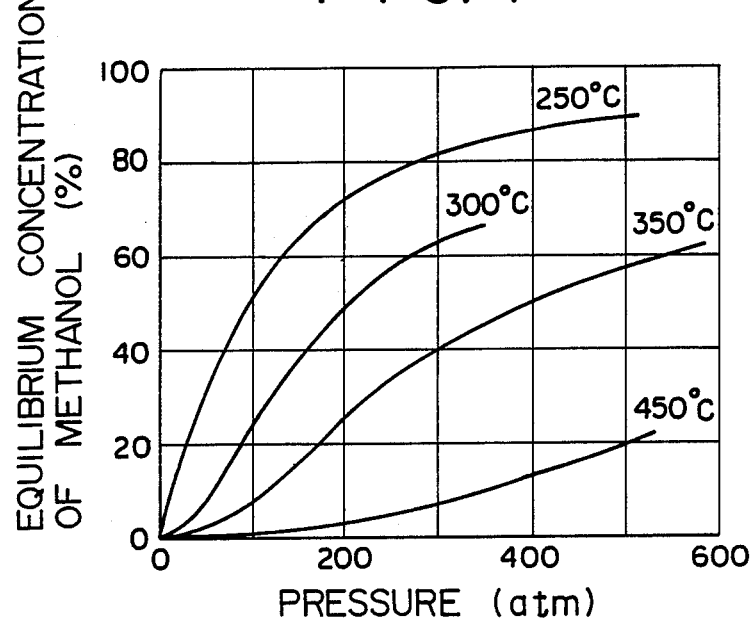
FIG. 1 is a graph showing a relation of pressure and temperature effect to an equilibrium concentration in a methanol synthesis reaction.
Figure 3:
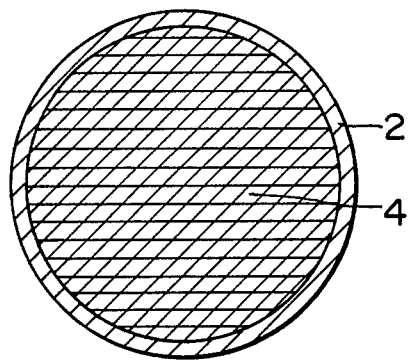
FIG. 3 is a horizontal section of the reaction vessel in FIG. 2.
Figure 4:
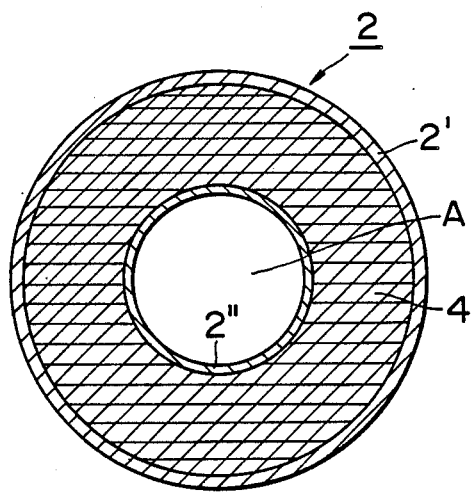
FIG. 4 is a horizontal section of a reaction vessel along line 4—4 of FIG. 5, according to the present invention.
Figure 2:
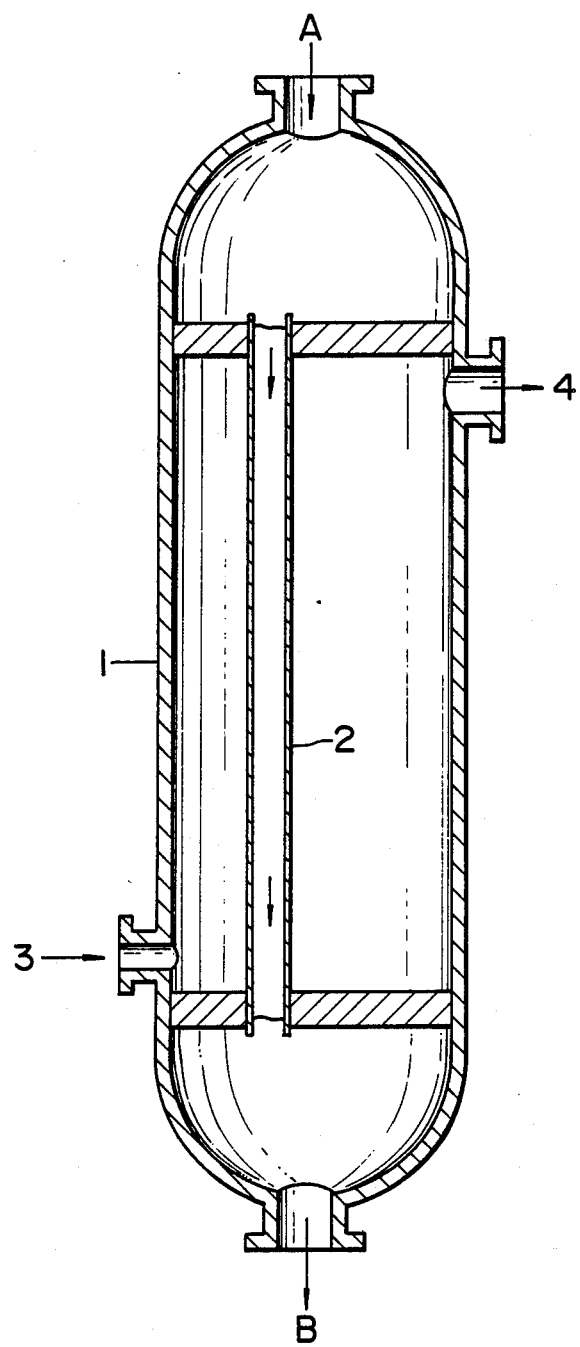
FIG. 2 is a vertical section of a conventional reaction vessel.
Figure 5:
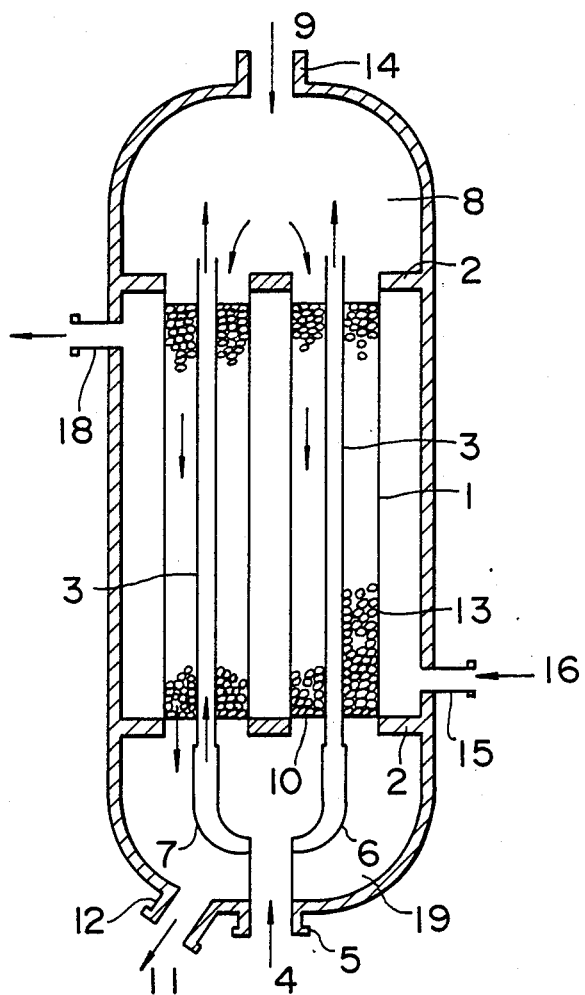
FIG. 5 is a vertical section of the reaction vessel according to the present invention.

FIG. 5 shows one example of a structure of a reaction vessel according to the present invention. A reaction pipe 1 is fixed at the opposite upper and lower ends thereof by two circular plates 90 and a central pipe 3 is disposed in the middle of each reaction pipe 1. A circular space defined between the reaction pipe 1 and the central pipe 3 is packed with a grainy catalyst to form a circular catalyst layer 13. An unreacted feed gas 40 is delivered from the unreacted feed gas nozzle 5 and reaches lower the central pipes 3 through the branch ducts 6, 7 to a mixing chamber 8 defined at the upper portion in the reaction vessel. Another cold unreacted feed gas 9 is introduced into the mixing chamber 8 through a nozzle 14 and is mixed with the unreacted feed gas coming out through the central pipes 3, and the resultant mixed gas is then guided to the circular catalyst layers 13.

The gas is caused to pass through the circular catalyst layers 13 and then reaches, through outlets 10 of the catalyst layers 13, a gathering chamber 19 defined at a lower portion in the reaction vessel, and the gas is afterward caused to run out through a reaction vessel outlet nozzle 12 as a reaction gas 11 from the reaction vessel.

A boiling liquid 16 for cooling the reaction pipe 1 from the outside surface thereof is introduced into the reaction vessel through an inlet nozzle 15 and discharged therefrom through an outlet nozzle 18 of the reaction vessel.

Figure 6:
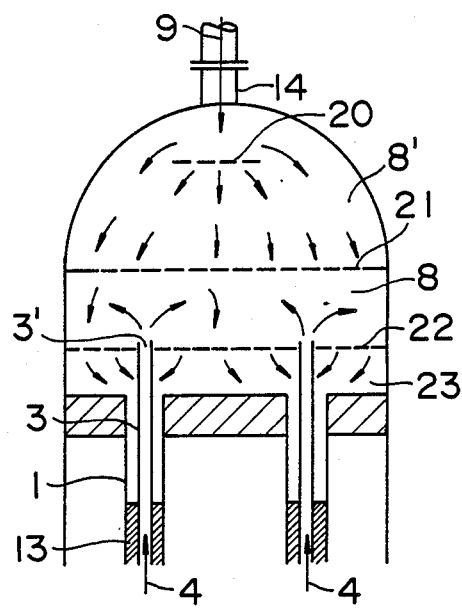
FIGS. 6 to 9 are vertical sections illustrating various embodiments of mixing chambers for the reaction vessel according to the present invention.

FIG. 6 shows another embodiment of the mixing chamber regarding the present invention. In this drawing, the unreacted feed gas 41 is heat exchanged with the circular catalyst layers 13 while flowing upward through the central pipes 3 in order to be heated and is then forwarded to the mixing chamber 8 through central pipe outlets 3'. On the other hand, the other cold unreacted feed gas 9 is introduced into the reaction vessel through the nozzle 14 and is hit against a dispersing plate 20 in order to be dispersed, and it is then caused to go into a dispersing chamber 8'. The gas is further forwarded via a dispersing plate 21 to the mixing chamber 8, where it is then mixed with the preheated unreacted feed gas 3'. The resultant mixed gas is caused to pass through a dispersing plate 22 in order to be mixed more uniformly and is guided to the catalyst layers 13 via a dealing chamber 23. In this case, the two dispersing plates 20 and 21 for the unreacted feed gas 9 are exhibited in this drawing, but the only one dispersing plate may be disposed.

Figure 7:
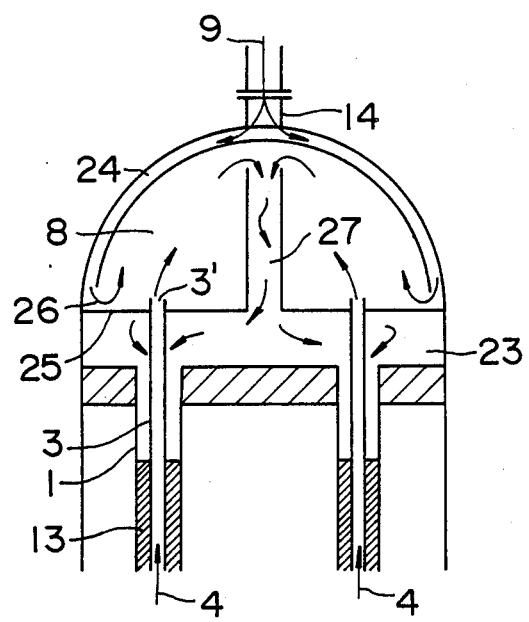

FIG. 7 shows still another embodiment of the mixing chamber, and in this embodiment, the unreacted feed gas 41 is heat exchanged with the circular catalyst layers 13 while flowing upward through the central pipes 3 and is then forwarded to the mixing chamber 8 via the central pipe outlets 3'. On the other hand, the other cold unreacted feed gas 9 is introduced into the reaction vessel via the nozzle 14 and is then caused to descend through a mirror plate space 24. Afterward, the gas 9 is guided via a space 26 confronted with a partition 25 to a mixing chamber 8, where it is mixed with the preheated unreacted feed gas 3'. The thus uniformly mixed gas is caused to pass through a mixing pipe 27 in order to be mixed more uniformly during its passage, and the gas is then guided to the dealing chamber 23 and afterward the catalyst layers 13.

Figure 8:
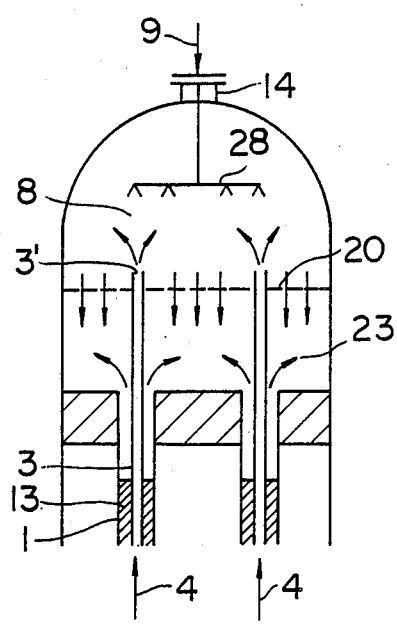

FIG. 8 shows a further embodiment of the mixing chamber, and in this embodiment, the unreacted feed gas 4 is heated by heat exchange with the circular catalyst layers 13 while flowing upward through the central pipes 3 and is introduced into the mixing chamber 8 via the central pipe outlets 3'. On the other hand, the other cold unreacted feed gas 9 is introduced into the reaction vessel through the nozzle 14 and is then jetted via a dispersing header 28 into the mixing chamber 8, where it is mixed with the preheated unreacted feed gas 3'. The thus mixed unreacted feed gas is caused to pass through the dispersing plate 20 in order to be mixed more uniformly at this time and is then introduced via the dealing chamber 23 into the catalyst layers 13.

Figure 9:
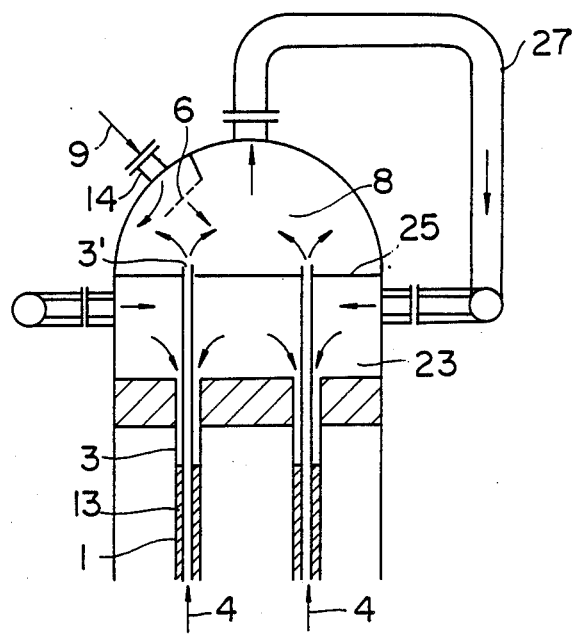

FIG. 9 shows a still further embodiment of the mixing chamber, and in this embodiment, the unreacted feed gas 4 is heated by heat exchange with the circular catalyst layers 13 while flowing upward through the central pipes 3 and is forwarded to the mixing chamber 8 via the central pipe outlets 3'. On the other hand, the other cold unreacted feed gas 9 is introduced into the reaction vessel through the nozzle 14 and is hit against a baffle 6, so that it is dispersed in the mixing chamber 8, where it is mixed with the preheated unreacted feed gas 3'. The thus mixed material gas is caused to pass through a mixing pipe 27 in order to be mixed more uniformly during its passage and is then guided to the dealing chamber 23 divided by a partition 25 and afterward the catalyst layers 13.

As a matter of course, in the one reaction vessel, a plurality of the reaction pipes packed with the catalyst may be disposed, but the one central pipe is disposed to the one reaction pipe. Each central pipe may be connected to one end of a connecting pipe, another end of which may be connected to a header. The connection of the central pipe with the connecting pipe and the connection of the header with the connecting pipe are suitably carried out in an optional manner such as a flange structure (bolt join) so as to be easily detached when needed.

POSSIBILITY OF INDUSTRIAL UTILIZATION

In contrast with the prior application (Japanese Patent Application No. 213724/1983; "double pipe type exothermic reaction vessel"), the present invention permits directly controlling a temperature of the unreacted feed gas at the circular catalyst layer inlets by introducing the cold gas into the upper portion of the reaction vessel, and can accomplish a more effective control particularly even for an abrupt temperature rise at the catalyst layer inlets at an early operation stage in which a catalyst activity is very great.

For this reason, the maximum temperature in the catalyst layer can be caused to fall without lowering a pressure of the boiling liquid which is a cooling medium, and a life span of the used catalyst particularly in the vicinity of the inlets can thus be prolonged.

As is definite from the foregoing, according to the present invention, the reaction temperature can be maintained within the range of proper levels in order to heighten a reaction efficiency, i.e., a concentration of the reaction product at a reaction vessel outlet, which fact is industrially very valuable. In addition thereto, in the reaction vessel of the present invention, the central pipes can be vibrated by means of a vibrator at the time of a catalyst packing operation, whereby the catalyst can be packed closely and firmly without leaving spaces therein and a pressure loss of each catalyst layer can thus be uniformized (uniformization of space velocity), which facts are also great advantages of the present invention.

In the case of "the double pipe type exothermic reaction vessel" of Japanese Patent Application No. 213724/1983 which has already been invented by the present inventors, the unreacted feed gas is introduced into the central pipes from their upper ends and is then discharged from the central pipes through the lower ends and the gas is also caused to flow through the circular catalyst layers downward from their upper ends in order to accomplish the reaction during its flow. Therefore, if a diameter of each catalyst grain is small and a space velocity of the gas is too high, the catalyst grains will be streamed and will consequently undergo mechanical wear. As a result, the pressure loss in each reaction pipe will be ununiformed and the space velocity will also be ununiformed, which fact will tend to deteriorate the performance. However, the present invention has the constitution that the gas is caused to flow through the catalyst-packed portions downward from above, and thus the occurrence of the above-mentioned problem can be restrained perfectly even if the space velocity is high.

As described above, the reaction vessel of the present invention can achieve a gas phase exothermic reaction by the use of the grainy solid catalyst and thus has an industrially great value. Besides, the present invention can be applied to uses other than the synthesis of methanol, and a composition of the gas, a kind and shape of the catalyst, a space velocity, a pressure and a temperature are not particularly restricted.

Although omitted in FIG. 5, there are known a structure of disposing the central pipes in the middle of the reaction pipes and a disposition, at the lower circular plate, of a member for preventing the catalyst from dropping, and the present invention does not intend to limit these constitutions. Also with regard to a diameter and length of each reaction pipe packed with the catalyst, a diameter and length of each central pipe, fins fixed on pipe surfaces to increase a heat transfer area, a formation of grooves, a material of the pipes and a shape of the baffle, they are not specified in the present invention. They are decided in accordance with many factors such as a pressure, a composition of the gas, a temperature, an amount of the reaction heat and a performance of the catalyst, and in the present invention, these factors are not restricted especially.

As described above, in the present invention, a part of the reaction heat of the gas which is reacting in the catalyst layers is given to the unreacted feed gas flowing through the central pipes by a heat transfer via walls of the central pipes in order to preheat the unreacted feed gas and to simultaneously cool the gas in the catalyst layers (temperature control). These effects satisfy the requirement of maintaining a temperature of the gas in the central pipes at a lower level than a reaction temperature. The remaining reaction heat is removed as an evaporation latent heat of water by a heat transfer to the pressurized water having a saturated temperature which is brought into contact with the outer surface of the reaction pipes, and the pressurized water vapor generated is taken out from the reaction vessel and is then used for another application. The heat transfer and the removal function of the reaction heat will not be accomplished naturally, if the temperature of the pressurized water is not set to a lower level than the reaction temperature. Accordingly, a pressure (saturated temperature) of the pressurized water should be decided suitably on the basis of a necessary amount of the heat to be transferred and an aimed reaction temperature.

As understood from the above, the present invention is desirable as a reaction vessel, for example, for methanol synthesis, which carries out the exothermic reaction of the gas by the use of the solid grainy catalyst and which requires the control of the reaction temperature to enhance its performance. Additionally, in the case of the present invention, since the structure is simple, there can be easily carried out design, manufacture, inspection, repair, catalyst filling and catalyst takeout, and the stability of operation is also excellent, and thus it can be believed that the present invention has an industially great value.

TEST FOR COMPARISON

According to the embodiment shown in FIG. 6, an example and comparative examples were carried out. With regard to a composition of a feed material gas, a space velocity of the feed material gas and a reaction pressure, they were common to the example and the comparative examples.

| Composition of feed material gas (mole %) | |
| --- | --- |
| $CO_2$ | 5.8 |
| CO | 9.6 |
| $H_2$ | 68.4 |
| $CH_4$ | 15.2 |
| $N_2$ | 0.6 |
| $H_2O$ | 0.0 |
| Methanol | 0.4 |
| Space velocity of feed gas | 6500 1/HR |
| Reaction pressure | 96 kg/cm$^2$ · G |

| | Example | Compar. Example 1 | Compar. Example 2 |
| --- | --- | --- | --- |
| Quench operation | Done | Not done | Not done |
| Rate (%) of quench gas amount to feed gas amount above inlets of all catalyst layers | 37 | 0 | 0 |
| Temp. (°C.) of material gas at inlet of central pipe | 150 | 150 | 150 |
| Temp. (°C.) of material gas at outlet of central pipe | 272 | 282 | 267 |
| Temp. (°C.) of quench gas | 150 | — | — |
| Temp. (°C.) of mixed gas | 227 | — | — |
| Temp. (°C.) at inlet of catalyst layer | 227 | 282 | 267 |
| Maximum temp. (°C.) in catalyst layer | 280 | 315 | 280 |
| Temp. (°C.) at outlet of catalyst layer | 250 | 250 | 235 |
| Temp. (°C.) of saturated pressurized water | 260 | 260 | 245 |
| Pressure (kg/cm$^2$ · G) of generated saturated | 47 | 47 | 36 |

-continued water vapor

In the example of the present invention, the unreacted feed gas coming out through the central pipes was mixed with a quench gas which was the cold unreacted feed gas in order to lower a temperature of the resultant mixed gas at the inlets of the catalyst layers. The effects thus obtained are set forth in the above table. In this Example, saturated pressurized water was used as a boiling liquid for cooling.

In Comparative Example 1, a temperature of the mixed gas at the inlets of the catalyst layers was 282° C. and a maximum temperature of the mixed gas in the catalyst layers was as high as 315° C. Especially at an early operation stage in which a catalyst activity is good, a temperature of the gas in the catalyst layers preferably is lower on the whole, since a life span of the catalyst can be prolonged. For this reason, in Comparative Example 2, the maximum temperature of the catalyst layers was maintained at 280° C. by lowering a pressure of the pressurized water which was a cooling medium. However, the present invention permits retaining the same maximum temperature as in Comparative Example 2 without lowering the pressure of the pressurized water.

The pressurized water which has been evaporated by a reaction heat is taken out in the form of water vapor from the reaction vessel and can be effectively utilized as a variety of energy sources, but in this case, needless to say, the higher the pressure of the water vapor is, the greater its value as energy is.

Therefore, it is clearly beneficial that the maximum temperature of the catalyst layer can be maintained at a predetermined level or less even at the early stage involving a good catalyst activity by employing the quench gas without lowering the pressure of the vapor to be recovered, as in Example of the present invention.

We claim:

1. A reactor comprising a reaction vessel, an inlet formed at one end of said reaction vessel for supplying unreacted feed gas, an inlet formed at the other end of said reaction vessel for supplying cold unreacted gas of a temperature lower than that of said first unreacted feed gas, a mixing chamber provided in upper part of said reaction vessel and communicating with said inlet for cold unreacted gas, a circular catalyst layer provided in middle of said reaction vessel, a gathering chamber provided in lower part of said reaction vessel, and a central pipe piercing and extending through said circular catalyst layer, the upper end of said central pipe being opened in said mixing chamber, the lower end thereof being connected to said inlet for unreacted feed gas and a coolant inlet and outlet being formed in said reaction vessel for supplying a coolant to the external circumference of said circular catalyst layer, and an outlet for reacted gas being formed in said gathering chamber wherein a dispersing plate is disposed between said cold unreacted feed gas introducing section and said circular catalyst layers.

2. A reactor comprising a reaction vessel, an inlet formed at one end of said reaction vessel for supplying unreacted feed gas, an inlet formed at the other end of said reaction vessel for supplying cold unreacted gas of a temperature lower than that of said first unreacted feed gas, a mixing chamber provided in upper part of said reaction vessel and communicating with said inlet for cold unreacted gas, a circular catalyst layer provided in middle of said reaction vessel, a gathering chamber provided in lower part of said reaction vessel, and a central pipe piercing and extending through said circular catalyst layer, the upper end of said central pipe being opened in said mixing chamber, the lower end thereof being connected to said inlet for unreacted feed gas and a coolant inlet and outlet being formed in said reaction vessel for supplying a coolant to the external circumference of said circular catalyst layer, and an outlet for reacted gas being formed in said gathering chamber wherein a dealing chamber is disposed between said mixing chamber and said circular catalyst layers.

3. The reaction vessel according to claim 2 wherein said mixing chamber is connected to said dealing chamber by a mixing pipe.

* * * * *